(12) United States Patent
McGowan et al.

(10) Patent No.: US 6,787,680 B2
(45) Date of Patent: Sep. 7, 2004

(54) WOUND DRESSING IMPERVIOUS TO CHEMICAL AND BIOLOGICAL AGENTS

(75) Inventors: Jeremy McGowan, Buckhannon, WV (US); Bruce Hewitt, Buckhannon, WV (US)

(73) Assignee: Jeremy D. McGowan, Buckhannon, WV (US)

( * ) Notice: Subject to any disclaimer, the term of this patent is extended or adjusted under 35 U.S.C. 154(b) by 301 days.

(21) Appl. No.: 10/076,167

(22) Filed: Feb. 15, 2002

(65) Prior Publication Data

US 2003/0163074 A1 Aug. 28, 2003

(51) Int. Cl.$^7$ ................................................. A61F 13/00
(52) U.S. Cl. .............................. 602/43; 602/3; 602/42; 602/54
(58) Field of Search ............................... 602/41, 42, 43, 602/52, 54; 604/385.01; 128/888, 889; 424/443–449

(56) References Cited

U.S. PATENT DOCUMENTS

| | | | |
|---|---|---|---|
| 4,390,519 A | * 6/1983 | Sawyer | 424/447 |
| 4,443,512 A | * 4/1984 | Delvaux | 428/162 |
| 4,538,603 A | * 9/1985 | Pawelchak et al. | 602/56 |
| 4,551,490 A | * 11/1985 | Doyle et al. | 524/22 |
| 4,578,071 A | * 3/1986 | Buell | 604/379 |
| 4,678,464 A | * 7/1987 | Holtman | 604/385.03 |
| 4,738,257 A | * 4/1988 | Meyer et al. | 602/48 |
| 4,743,499 A | * 5/1988 | Volke | 428/317.3 |
| 4,762,124 A | * 8/1988 | Kerch et al. | 604/307 |
| 4,867,748 A | * 9/1989 | Samuelsen | 604/336 |
| 4,936,839 A | * 6/1990 | Molee et al. | 604/378 |
| 4,977,892 A | * 12/1990 | Ewall | 602/52 |
| 5,185,009 A | * 2/1993 | Sitnam | 604/364 |
| 5,267,992 A | * 12/1993 | Van Tilburg | 604/387 |
| 5,350,370 A | * 9/1994 | Jackson et al. | 604/367 |
| 5,447,505 A | * 9/1995 | Valentine et al. | 604/304 |
| 5,643,189 A | * 7/1997 | Masini | 602/58 |
| 5,645,849 A | * 7/1997 | Pruss et al. | 424/426 |
| 5,681,579 A | * 10/1997 | Freeman | 424/448 |
| 5,968,001 A | * 10/1999 | Freeman | 602/42 |
| 6,023,008 A | * 2/2000 | Mahoney et al. | 602/56 |
| 2002/0091368 A1 | * 7/2002 | LaVon et al. | 604/385.14 |

* cited by examiner

Primary Examiner—Kim M. Lewis

(57) ABSTRACT

The skin contacting layer of the present invention utilizes a skin contacting occlusive layer that is provided with an uninterrupted border of pressure sensitive occlusive adhesive that encompasses the wound, thereby providing a chemical and biological resistant seal to the skin for containment of body fluids within the absorbent region of the dressing. This arrangement will prevent the migration of body fluids beyond the chemical land biological resistant barriers of the dressing and provide a safe means of minimizing exposure to body fluids, thus reducing the possibility of contact with contagions within said body fluids by attending personnel. Due to the fact the loss of body fluids into chemical and biological protective garment will decrease the garment's effectiveness, the present invention may also be used to treat persons who are injured in a chemically or biologically contaminated environment. The present invention will aid in preventing body fluids both from contacting with attendant personnel and from migrating past the borders of the absorbent region of the bandage into the material of the protective garment.

4 Claims, 2 Drawing Sheets

4.

5.

6.

WOUND DRESSING IMPERVIOUS TO CHEMICAL AND BIOLOGICAL AGENTS

BACKGROUND OF THE INVENTION

The present invention relates to bandages that are used for containment of and prevention of migrating body fluids. Migrating body fluids are detrimental to a chemical and biological resistant garment and can increase the absorption of chemicals through the skin and may further injure/incapacitate the wounded individual. It is also beneficial to contain body fluids within the dressing to prevent unnecessary exposure to body fluids by attendant personnel.

It is an object of the present invention to increase the capacity and rate of fluid uptake within an occlusive wound dressing, and to contain and prevent the migration of body fluids through the protective layers of a chemically and biologically resistant garment.

It is an object of the present invention to contain and prevent the migration of body fluids through the perimeter of the occlusive dressing thereby controlling exposure to body fluid by attending personnel.

It would be a significant advancement in the treatment of persons wounded in a chemically or biologically contaminated environment to be treated with a wound dressing capable of rapidly providing a sealed wound environment that is impervious to chemical and biological agents while protecting the surrounding area by patching any damage to the chemical and biological protective garment. It would also be a significant advance in the isolation of blood borne pathogens and other bodily fluid contagions by treating persons with a wound dressing capable of containing bodily fluids within a layer impervious to the passage of any contagions that may be present thereby preventing attending persons from exposure to said fluids contagions and pathogens.

Much effort has been directed to enhancing the uptake, capacity and containment of bodily fluids within this chemical and biological resistant wound dressing, while paying particular attention to the ability to eliminate migration of bodily fluids beyond the absorbent areas of the dressing; this is necessary to prevent more rapid absorption of chemicals through the fabric of the chemical resistant garment preventing further injury or incapacitation to the wounded person and to prevent the escape of bodily fluids into the surrounding environment thereby protecting attending persons from contagions and pathogens possibly contained in the bodily fluids of the wounded person. In response to this need, absorbent layers in wound dressings have been provided with hydrocolloids, super absorbents, and synthetic materials that have extensive capacities to absorb bodily fluids. By incorporating these technologies with an occlusive layer impervious to both chemical and biological agents provided with an uninterrupted border of pressure sensitive adhesive, bodily fluids may be contained against the persons body without leakage, and a protective outer patch may be applied to increase the integrity of the damaged chemical and biological resistant garment.

SUMMARY OF THE INVENTION

The present invention is directed towards wound dressings impervious to chemical and biological agents therefore designed for use in chemically and biologically contaminated environments and for wound dressing designed for use in protecting attending persons from contamination of biological contagions from the wounded person, having a designated absorbent region defined by liquid resistant materials that enable the uptake and storage of bodily fluids within the wound dressing, while simultaneously containing and preventing the migration of bodily fluids from the occlusive dressing thereby preventing exposure to any contagion or pathogen that may be present in said bodily fluid.

BRIEF DESCRIPTION OF THE DRAWINGS

The following drawings in which like reference characters indicate like parts are illustrative of embodiments of the invention and are not intended to limit the invention as encompassed by the claims forming part of the application.

DETAILED DESCRIPTION OF THE INVENTION

The present invention is generally directed to a wound dressing comprised of an external occlusive layer, a lower skin-contacting substrate layer and an absorbent layer there between for the uptake of body fluids such as blood or wound exudate. An absorbent region is enclosed within and defined by an adhesive seal placed around the perimeter of the skin contacting layer. The seal prevents migration of the body fluid from the absorbent region while retaining positive healing environment about the wound.

Figure 1:
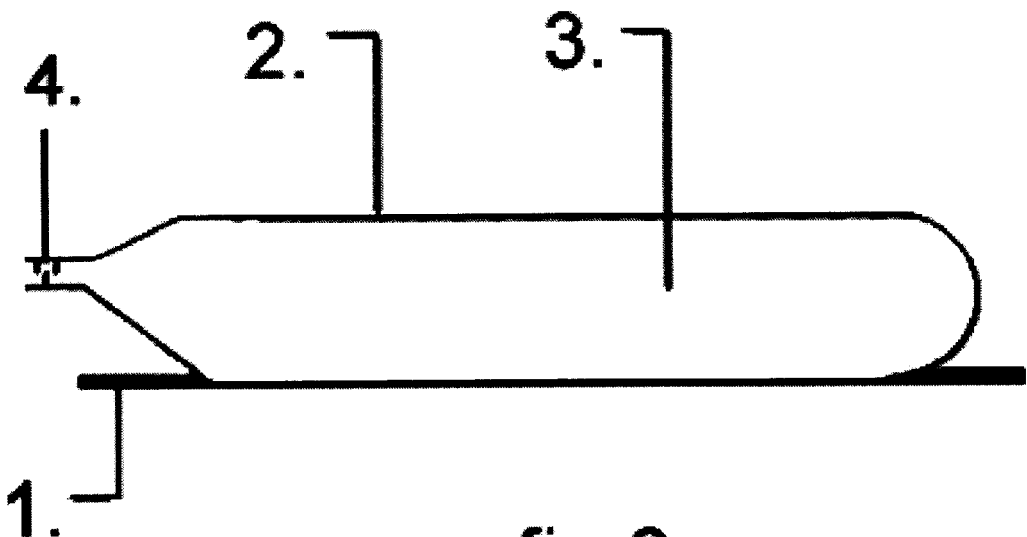
FIG. 1 is a cross-sectional side view of one embodiment of the present invention.
Figure 2:
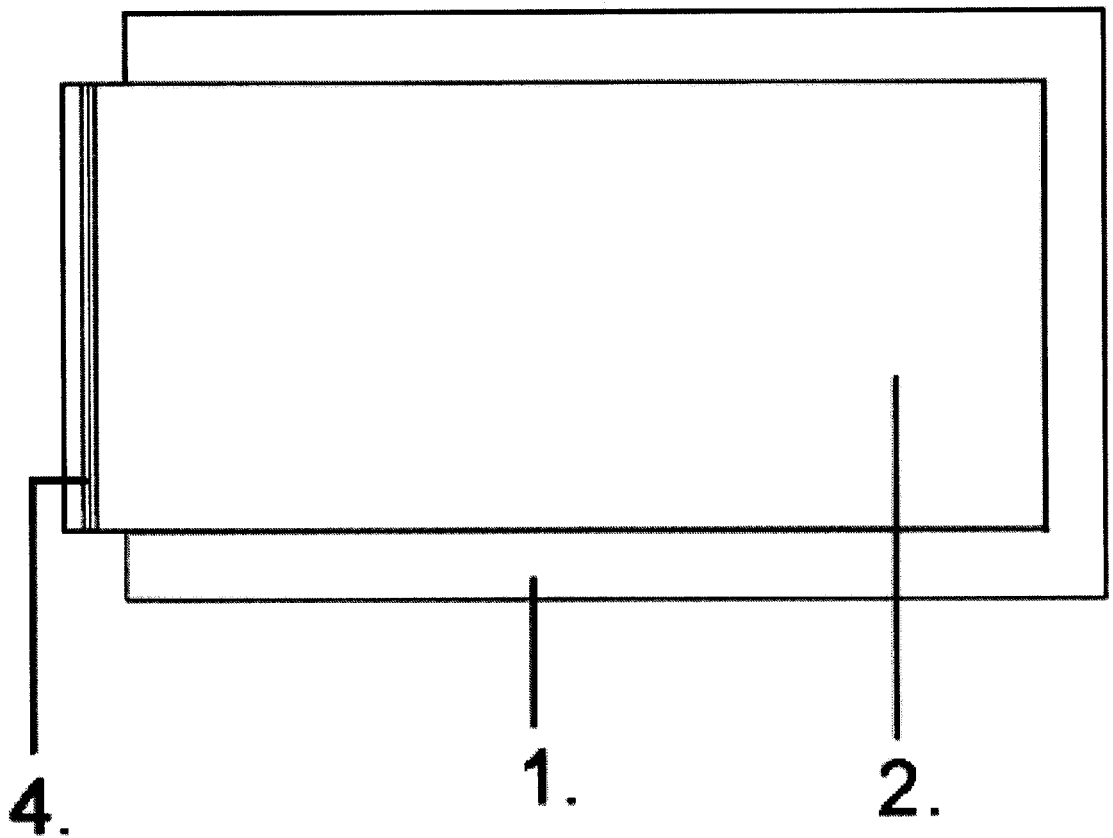
FIG. 2 is a top view of the embodiment of the invention shown in FIG. 1.
Figure 3:
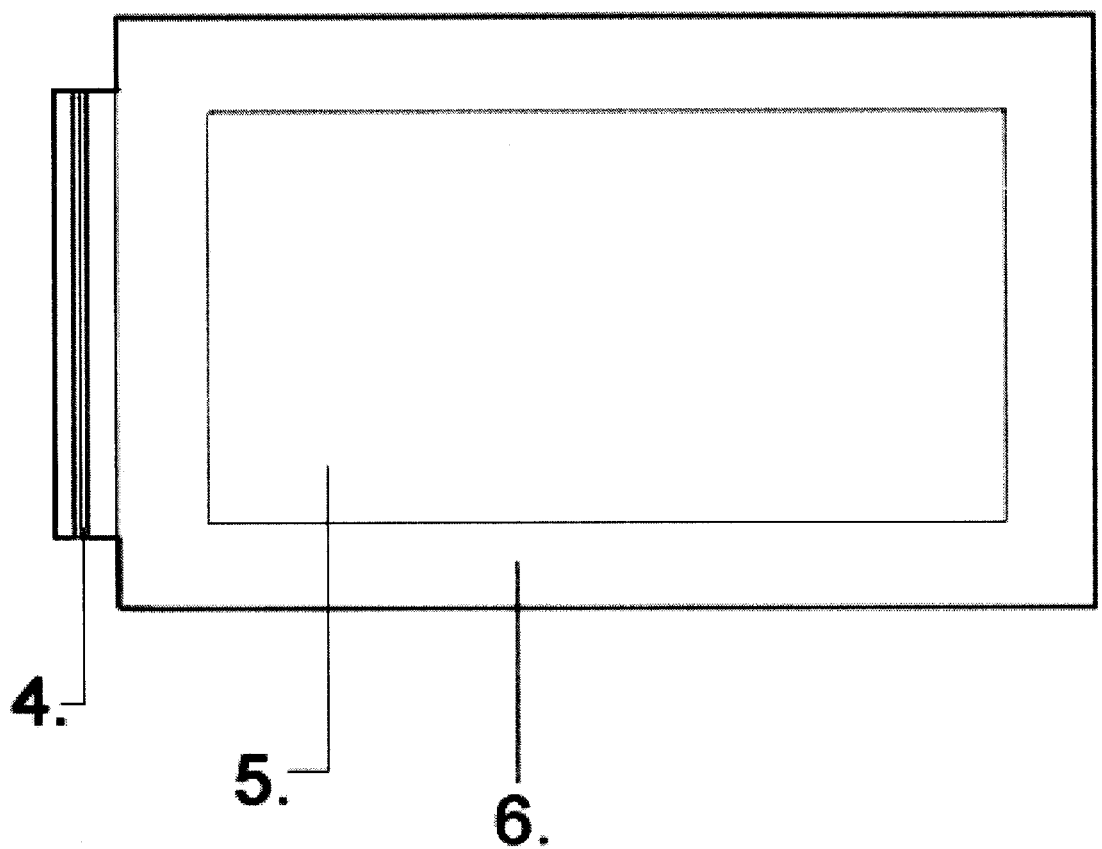
FIG. 3 is a bottom view the embodiment of the invention shown in FIG. 1.

Referring to FIGS. 1, 2 and 3, there is an embodiment of the invention shown that employs an adhesive seal that is applied to the skin or clothing surrounding the wound which defines the absorbent region of the dressing, the skin contacting substrate layer is placed directly over the wound to provide for uptake of the bodily fluids into the absorbent layer.

The wound dressing (FIG. 3) includes a skin contacting substrate [5] having an upper occlusive layer (FIG. 1) [2] and a lower skin-contacting layer (FIG. 3) [5]. An absorbent region (FIG. 1) [3] as more fully described hereinafter is positioned between the occlusive layer (FIG. 1) [2] and the skin contacting layer (FIG. 1) [1]. The absorbent region (FIG. 1) [3] is capable of up-taking body fluids and storing the same away from the wound area. The seal (FIG. 1) [4] and the adhesive border (FIG. 3) [6] are sufficient to substantially prevent body fluids, such as blood or wound exudate from migrating outside the absorbent region (FIG. 1) [3]. The adhesive border (FIG. 3) [6] in conjunction with the occlusive layer (FIG. 1) [2] forms a barrier that is impervious to both chemical and biological agents such as, but not limited to; anthrax; tabun (o-ethyl dimethylamidophosphorylcyanide); sarin (isopropyl methylphosphonofluoridate); soman (pinacolyl methylphosphonofluoridate); cyclohexyl methylphosphonofluoridate; o-ethyl s-diisopropylaminomethyl methylphosphonothiolate; mustard agents (bis- (2-chloroethyl) sulphide) and is adapted for maintaining the wound in a positive healing environment while preventing the uncontrolled loss of body fluids and uptake of chemical or biological contaminants into the wounded area.

As shown in FIGS. 1 and 2, the wound dressing, particularly the substrate layer (FIG. 3) [5] is circumscribed by an adhesive border (FIG. 3. The seal can be formed by applying energy to the wound dressing or by the application of a substance which alone or through the application of pressure can form a desirable seal. In a preferred form of the invention, the seal is formed by the application of adhering an occlusive material around the periphery of a wound thereby containing bodily fluids within the occlusive bandage. The adhesive provides a barrier impervious to chemical and biological agents by sealing together portion of the skin contacting occlusive layer to the skin (FIG. 1) [1], the absorbent layer (FIG. 1) [3] and the skin-contacting substrate layer (FIG. 3) [5] to form the absorbent region (FIG. 1) [3]. The preferred seals are formed from the application of an adhesive to the skin or clothing. It is essential that the materials forming the wound dressing be sealable by the type of materials which is employed as explained hereinafter.

Alternatively, the seal can be formed from a substance that is impervious to the passage of body fluids. Examples of such materials include adhesives, caulking compounds, water impervious polymers such as ethylene vinyl acetate compounds and butyl compounds. The seals can be formed from such materials by applying the same to the wound dressing during manufacture and allowing the material to set. In another method water impervious materials are coated onto the fibers or other components of the wound dressing and then energy is applied (e.g. thermal or ultrasonic energy) or the fibers are compressed to form the seal.

The wound dressing (FIG. 2) can comprise a plurality of seals to form the absorbent region (FIG. 1) [3]. There is shown an embodiment of the wound dressing in which two seals (FIG. 2) [4] and (FIG. 3) [6] are employed to contain the absorbent region within the occlusive outer layer (FIG. 1) [2] from the remaining portion of the wound dressing. The seals (FIG. 3) [4] and (FIG. 3) [6] may be formed by any of the same methods described above and may each be formed of the same or different methods. For example, the adhesive border (FIG. 3) [6] seal may be formed by the application of an adhesive to the skin and the dressing seal closure (FIG. 1) [4] may be formed of a different method such as by the use of a tongue and groove sealant system constructed of a chemical and biological impervious sealing material.

Multiple absorbents pads may be added or replaced when the amount of body fluid expected to be absorbed exceeds the absorbent capacity of the currently contained absorbents. The dressing seal closure (FIG. 1) [4] provides additional protection against migration of the body fluid from the absorbent region (FIG. 1) [3].

The shape of the adhesive border (FIG. 3) [6] is unlimited so long as the adhesive border restricts chemical and biological contaminant access to the absorbent region and prevents the passage of body fluids from entering the environment. The shape of the adhesive border can be circular, rectangular, in the form of a square, a polygon or can be irregularly shaped.

The composition of all occlusive layers (FIG. 1) [2], (FIG. 1) [1] can vary so long as there is an outer occlusive layer that is impervious to chemical and/or biological substances such as, but not limited to; anthrax; tabun (o-ethyl dimethylamidophosphorylcyanide); sarin (isopropyl methylphosphonofluoridate); soman (pinacolyl methylphosphonofluoridate; cyclohexyl methylphosphonofluoridate; o-ethyl s-diisopropylaminomethyl methylphosphonothiolate; mustard agents (bis- (2-chloroethyl) sulphide), and a substrate layer (FIG. 3) [5] and an absorbent layer there between (FIG. 1) [3] circumscribed by at least one seal (FIG. 3) [6] the wound dressing can therefore include a variety of absorbent materials and occlusive skin contacting materials.

It is an essential feature of the present invention that the wound dressing be capable of containing and absorbing body fluids in a designated absorbent region (FIG. 1) [3] while preventing the migration of body fluids or harmful chemical or biological substances through the occlusive layer (FIG. 1) [2], while maintaining the wound area in a positive healing environment. Thus, the absorbent region (FIG. 1) [3] must comprise the combination of materials that will promote fluid absorption and wound healing. The amount of the body fluid absorbing materials within the absorbent region (FIG. 1) [3] may vary according to the amount of body fluids that must be absorbed or contained.

A preferred composition of the wound dressing of the present invention is shown in FIGS. 1, 2, and 3. Referring first to FIG. 1, the wound dressing includes a skin-contacting layer [1], an absorbent layer [3] and an occlusive layer [2]. An adhesive border (FIG. 3) [6] is provided to the skin-contacting layer (FIG. 1) [1] to isolate the absorbent region (FIG. 1) [3], and to maintain placement of the skin contacting substrate (FIG. 3) [5] over the wound that aids in the uptake of bodily fluids through a permeable membrane.

The substrate layer (FIG. 3) [5] is the layer that remains in contact with the wound during application of the wound dressing. In accordance with the present invention, the substrate layer is made of a permeable material that serves to protect the wound dressing while allowing moisture or bodily fluids to pass there through into the absorbent region (FIG. 1) [3].

The skin-contacting layer (FIG. 01) [1] is provided with an adhesive border (FIG. 3) [6], with an optional skin-compatible adhesive thereon. When an adhesive is not used, the wound dressing may be taped or wrapped in place. The adhesive may be applied to the entire perimeter of the wound (FIG. 3) [6] but should not overlie the wound.

An adhesive is preferably placed on the outside border of the skin-contacting layer (FIG. 1) [1]. The adhesive composition may be any suitable adhesive such as one based on a high molecular weight polyisobutylene or an acrylic based adhesive. The adhesive may include a homogeneous blend of one or more pressure sensitive adhesive materials and one or more natural or synthetic polymers capable of developing elastomeric properties when hydrated such as gluten and long chain polymers of methyl vinyl ether/maleic acid. The composition may also include one or more water-soluble hydrocolloid gums and may additionally include one or more water swellable cohesive strengthening agents. One or more thermoplastic elastomers may be included with the pressure sensitive adhesive materials. Additionally, any form of adhesive may be used as long as the minimum requirements are adhered to as stated above.

In a preferred form of the invention, the absorbent material is comprised of a thermoplastic material such as polyolefin, or a polyester. The preferred polyolefin is polypropylene. In a preferred form of the invention, the absorbent layer (FIG. 1) [3] comprises a matrix of polypropylene with hydrocolloids and/or superabsorbents dispersed therein. The purpose of the hydrocolloids and superabsorbents is to trap fluid within the polymeric matrix and enable the raped uptake of said fluids.

As shown specifically in FIG. 1, the wound dressing has an outer occlusive layer (FIG. 1) [2], that is equipped with an air-tight closure (FIG. 1) [4] that may be repeatedly opened and resealed to replace or add absorbent materials without disturbing the healing process of the wound. The occlusive layer (FIG. 1) [2] has an upper or outer surface area that is impervious to chemical and/or biological agents such as, but not limited to; anthrax; tabun (o-ethyl dimethylamidophosphorylcyanide); sarin (isopropyl methylphosphonofluoridate); soman (pinacolyl methylphosphonofluoridate); cyclohexyl methylphosphonofluoridate; o-ethyl s-diisopropylaminomethyl methylphosphonothiolate; mustard agents (bis- (2-chloroethyl) sulphide) that is exposed to the atmosphere and an inner surface which faces the absorbent layer (FIG. 1) [3]. The occlusive layer (FIG. 1) [2] is comprised of materials that are generally impervious to fluid, gas and vapor transmission.

The skin-contacting layer (FIG. 1) [1] is to be bonded to the occlusive layer (FIG. 1) [2], with suitable adhesives that are impervious to fluid transmission and are not soluble when exposed to bodily fluids.

The hydrocolloid materials useful for the adhesive on the skin-contacting layer include any water soluble gum (e.g. pectin, guar gum, xantham gum), gelatin, carboxymethylcellulose (CMC), such as sodium CMC, sodium or calcium alginates, polysaccharides and the like.

The superabsorbent materials useful for the absorbent region (FIG. 1) [3] may be in any suitable form. Typical superabsorbents include starch grafted copolymers of acrylate salts, starch grafted copolymers of acrylamide salts, polyacrylate salts and the like, including mixtures thereof. Superabsorbent materials and composites are easily prepared or commercially available. The superabsorbent web may also be formed by needle punching processes. The superabsorbent may also be a delayed release web superabsorbent.

We claim:

1. A highly absorbent wound dressing comprising:
an upper occlusive layer impervious to biological and chemical agents such as, but not limited to: anthrax; tabun (o-ethyl dimethylamidophosphorylcyanide); sarin (isopropyl methylphosphonofluridate); soman (pinacolyl methylphosphonofluoridate); cyclohexyl methylphosphonofluoridate; o-ethyl s-diisopropylaminomethyl methylphosphonothiolate; and mustard agents (bis-(2-chloroethyl) sulphide), a skin-contacting layer and at least one pad of alginate fibers removably enclosed there between, wherein the alginate fibers have an absorbency of at least 40 G of deionized water per gram of pad, and a border comprising a layer of uninterrupted pressure-sensitive adhesive around the skin contacting layer, thereby preventing the migration of bodily fluids past the dressing.

2. The wound dressing of claim 1, wherein the dressing is designed to cover a wound and the adhesive border is designed to adhere to skin surrounding a wound, thereby containing bodily fluids within the dressing, while preventing chemical or biological agents from entering the wound.

3. The wound dressing of claim 1, further including a means for removably fastening the occlusive layer and the skin-contacting layer together to replace or add additional pads, to insert other substance such as wound healing substances, to seal in bodily fluids with possible contagions and to seal out chemical or biological contaminants from the wound from contacting the surrounding skin.

4. The wound dressing of claim 1, wherein the wound dressing is designed to cover a wound and the adhesive border is designed to adhere to clothing surrounding a wound, thereby containing bodily fluids within the dressing and increasing the integrity of a chemical and biological resistant garment.

* * * * *